US012559775B2

(12) United States Patent
Trego et al.

(10) Patent No.: US 12,559,775 B2
(45) Date of Patent: Feb. 24, 2026

(54) METHODS AND COMPOSITIONS FOR CELL-FREE BIOLOGICAL REACTIONS

(71) Applicant: Synvitrobio, Inc., San Francisco, CA (US)

(72) Inventors: Kelly S. Trego, San Francisco, CA (US); Louis E. Metzger, IV, San Francisco, CA (US); Abel C. Chiao, San Francisco, CA (US); Zachary Z. Sun, San Francisco, CA (US); Dan E. Robertson, IV, San Franciso, CA (US); Benjamin Mohr, San Franciso, CA (US)

(73) Assignee: SYNVITROBIO, INC., San Leandro, CA (US)

( * ) Notice: Subject to any disclaimer, the term of this patent is extended or adjusted under 35 U.S.C. 154(b) by 967 days.

(21) Appl. No.: 17/437,288

(22) PCT Filed: Mar. 9, 2020

(86) PCT No.: PCT/US2020/021763
§ 371 (c)(1),
(2) Date: Sep. 8, 2021

(87) PCT Pub. No.: WO2020/185708
PCT Pub. Date: Sep. 17, 2020

(65) Prior Publication Data
US 2022/0162651 A1       May 26, 2022

Related U.S. Application Data

(60) Provisional application No. 62/815,445, filed on Mar. 8, 2019.

(51) Int. Cl.
*C12P 7/42*        (2006.01)
*C07K 14/435*      (2006.01)

(52) U.S. Cl.
CPC .......... *C12P 7/42* (2013.01); *C07K 14/43504* (2013.01)

(58) Field of Classification Search
CPC ............ C12N 15/8261; C12N 15/8247; C12N 15/8273; C12N 5/04; C12N 5/16; C12N 2330/50; C12N 15/81; Y02A 40/146
USPC ....................................... 435/419
See application file for complete search history.

(56) References Cited

U.S. PATENT DOCUMENTS

| | | | |
|---|---|---|---|
| 10,612,031 | B2 * | 4/2020 | Krishna et al. |
| 2016/0160237 | A1 | 6/2016 | Burgess et al. |
| 2017/0120237 | A1 | 5/2017 | McCully et al. |
| 2017/0159017 | A1 | 6/2017 | Liu et al. |
| 2018/0245087 | A1 * | 8/2018 | Krishna et al. |
| 2019/0276852 | A1 | 9/2019 | Choi et al. |

FOREIGN PATENT DOCUMENTS

| | | |
|---|---|---|
| WO | 2010/074760 A1 | 7/2010 |
| WO | 2016/008937 A1 | 1/2016 |

OTHER PUBLICATIONS

Davos et al., (Proteins: Structure, Function and Genetics, 2000, vol. 41: 98-107.*
Wristlock et al., (Quarterly Reviews of Biophysics 2003, vol. 36 (3): 307-340.*
Kwiatkowski et al., (Biochemistry 38:11643-11650, 1999.*
Kisselev L., (Structure, 2002, vol. 10: 8-9.*
International Search Report and Written Opinion in PCT International Application No. PCT/US2020/021763 mailed Jun. 9, 2020.
Buntru, 2014, Tobacco BY-2 cell-free lysate: an alternative and highly-productive plant-based in vitro translation system, BMC Biotechnoloy 14(1):37.
Chiao, 2016, Development of prokaryotic cell-free systems for synthetic biology, bioRxiv, p. 048710.
Extended European Search Report issued in European Application No. 20769308.6, date of mailing: Jan. 16, 2023, 9 pages.
International Search Report and Written Opinion issued in International Application No. PCT/US2020/021763, date of mailing: Jun. 9, 2020, 13 pages.
Jewett, 2004, Mimicking the *Escherichia coli* cytoplasmic environment activates long-lived and efficient cell-free protein synthesis, Biotechnol Bioeng, 86(1):19-26.
Karim, 2016, A cell-free framework for rapid biosynthetic pathway prototyping and enzyme discovery, Metab Eng 36:116-126.
Kelwick, 2016, Development of a Bacillus subtilis cell-free transcription-translation system for prototyping regulatory elements, Metab Eng 38:370-381.
Kigawa, 1999, Cell-free production and stable-isotope labeling of milligram quantities of proteins, FEBS Lett, 442 (1):15-9.
Kim, 2001, Regeneration of adenosine triphosphate from glycolytic intermediates for cell-free protein synthesis, Biotechnol Bioeng, 74(4):309-316.
Komoda, 2004, Replication of plant RNA virus genomes in a cell-free extract of evacuolated plant protoplasts, Proceedings of the National Academy of Sciences of the United States of America, 101(7): 1863-1867.
Niederholtmeyer, 2015, Rapid cell-free forward engineering of novel genetic ring oscillators, eLife.
Opgenorth, 2014, A synthetic biochemistry molecular purge valve module that maintains redox balance, Nature Communications, 5(4113), 8 pages.

(Continued)

*Primary Examiner* — Tekchand Saidha
*Assistant Examiner* — Mohammad Y Meah
(74) *Attorney, Agent, or Firm* — Brown Rudnick LLP; Adam M. Schoen

(57)         ABSTRACT

Compositions and methods disclosed herein relate to improved in vitro cell-free systems for various biological reactions. In one aspect, a composition of the present disclosure includes: a cell-free extract derived from an organism; a nucleic acid; and an organelle that is heterologous to the organism.

12 Claims, 11 Drawing Sheets

(56)                    References Cited

OTHER PUBLICATIONS

Shin, 2012, An *E. coli*Cell-Free Expression Toolbox: Application to Synthetic Gene Circuits and Artificial Cells, ACS Synth Biol, 1(1):29-41.

Sun, 2013, Protocols for Implementing an *Escherichia coli* Based TX-TL Cell-Free Expression System for Synthetic Biology, Journal of Visualized Experiments, 79(e50762), 14 pages.

Sun, 2014, Linear DNA for Rapid Prototyping of Synthetic Biological Circuits in an *Escherichia coli*Based TXTL Cell-Free System, ACS Synth Biol, 3(6):387-397.

Takahashi, 2015, Characterizing and prototyping genetic networks with cell-free transcription-translation reactions, Methods, 86:61-72.

Thompson, 1984, Coupled transcription—translation in extracts of Streptomyces lividans, Molecular and General Genetics MGG, 195(1-2):39-43.

* cited by examiner

Preparation of Tobacco BY-2 cell extracts:

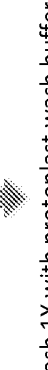

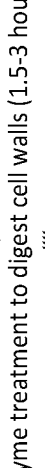

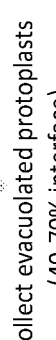

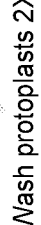

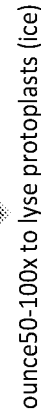

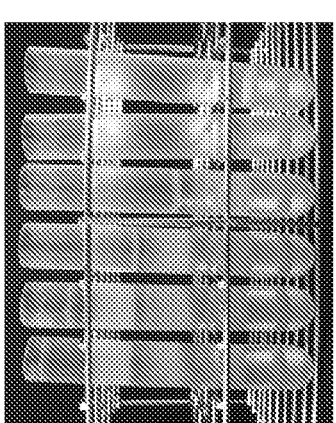

BY-2 cells, grown 4 days after 5% split

Wash 1X with protoplast wash buffer

Enzyme treatment to digest cell walls (1.5-3 hours)

Wash 2X with protoplast wash buffer

Percoll gradient to remove vacuole-rich vesicles and undivided protoplasts

Collect evacuolated protoplasts (40-70% interface)

Wash protoplasts 2X

Add 4 volumes translation buffer (ice)

Dounce50-100x to lyse protoplasts (ice)

Centrifuge lysates and recover the supernatant (=BYL)

FIG. 3

Isolation of Mitochondria from Plant Cell Culture 5-7 day old cultures

⇩

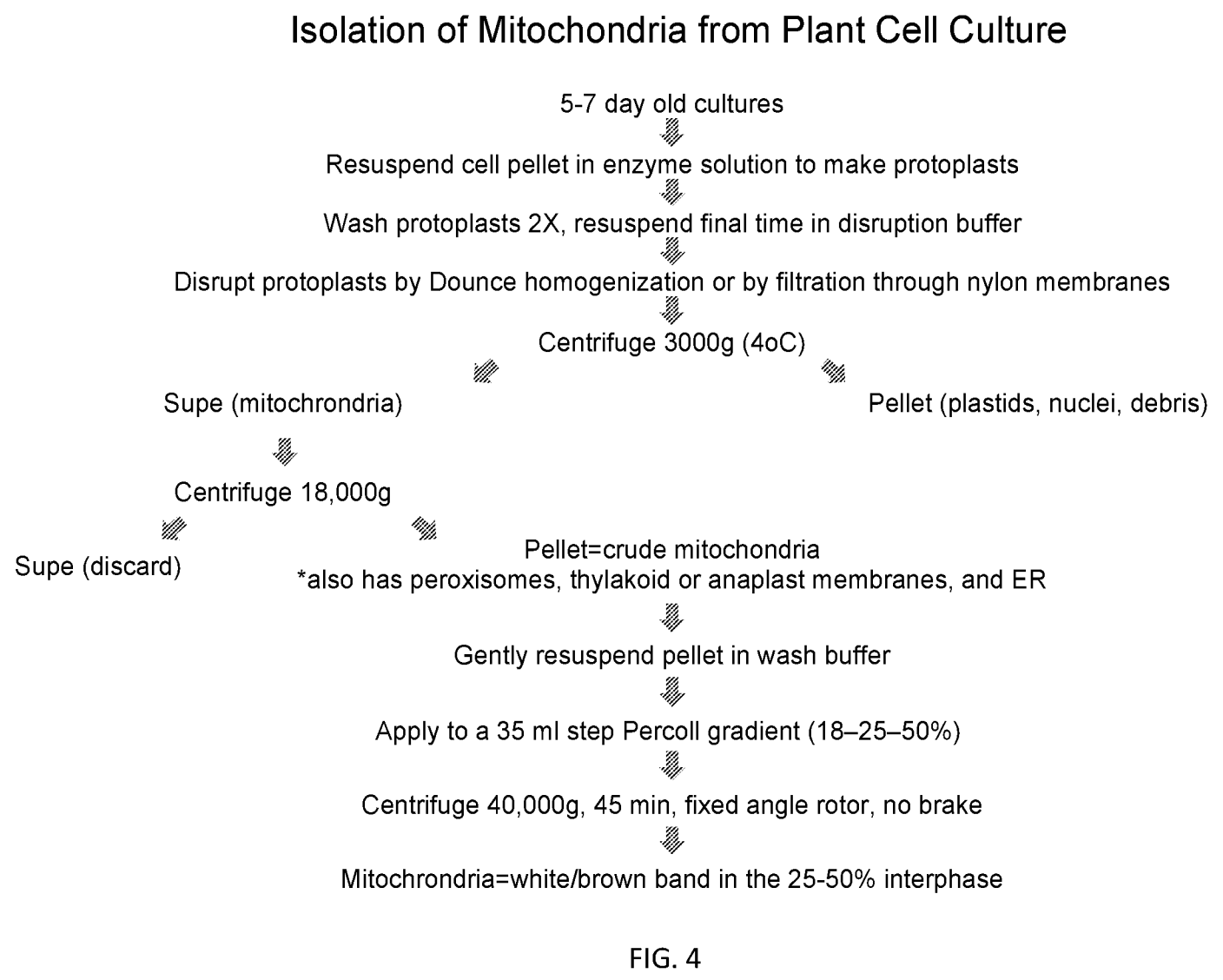

Resuspend cell pellet in enzyme solution to make protoplasts

⇩

Wash protoplasts 2X, resuspend final time in disruption buffer

⇩

Disrupt protoplasts by Dounce homogenization or by filtration through nylon membranes

⇩

Centrifuge 3000g (4oC)

⇩

Pellet (plastids, nuclei, debris)

Supe (mitochrondria)

⇩

Centrifuge 18,000g

⇩

Supe (discard)

Pellet=crude mitochondria

*also has peroxisomes, thylakoid or anaplast membranes, and ER

⇩

Gently resuspend pellet in wash buffer

⇩

Apply to a 35 ml step Percoll gradient (18–25–50%)

⇩

Centrifuge 40,000g, 45 min, fixed angle rotor, no brake

⇩

Mitochrondria=white/brown band in the 25-50% interphase

FIG. 4

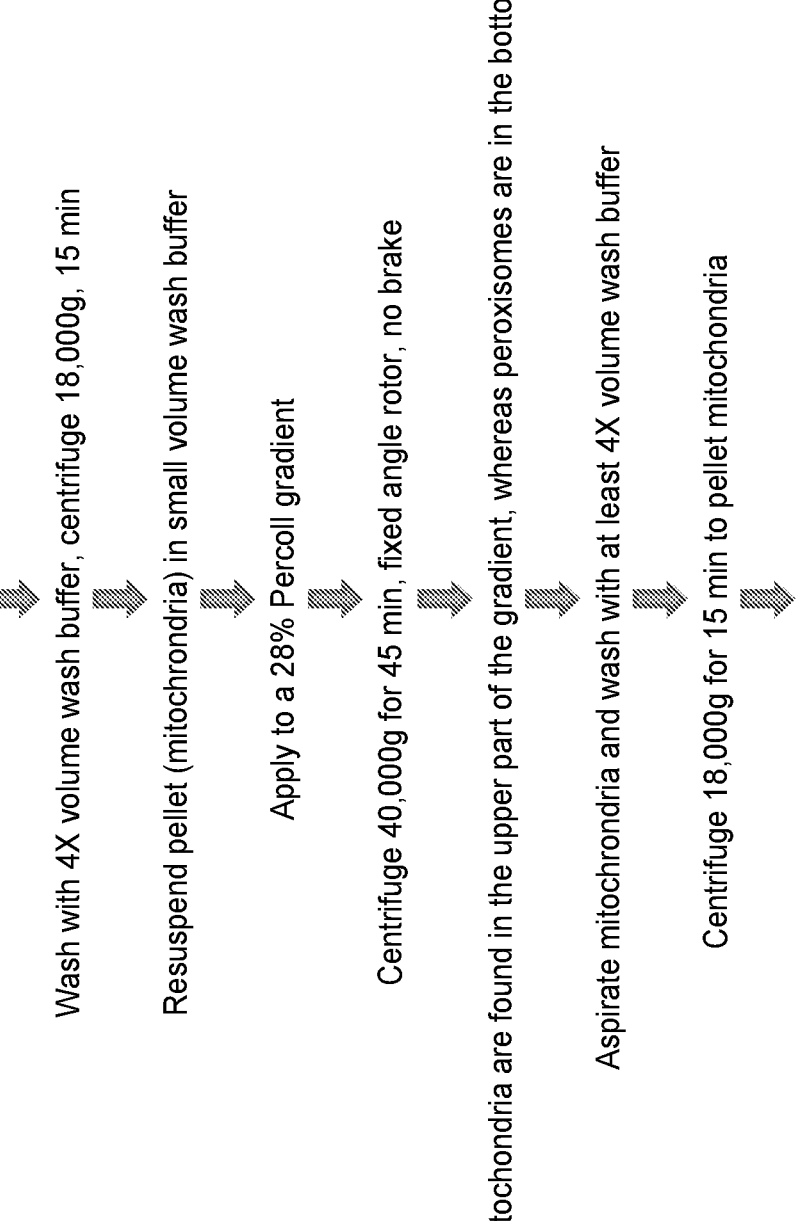

Wash with 4X volume wash buffer, centrifuge 18,000g, 15 min

Resuspend pellet (mitochrondria) in small volume wash buffer

Apply to a 28% Percoll gradient

Centrifuge 40,000g for 45 min, fixed angle rotor, no brake

Mitochondria are found in the upper part of the gradient, whereas peroxisomes are in the bottom Aspirate mitochrondria and wash with at least 4X volume wash buffer Centrifuge 18,000g for 15 min to pellet mitochondria Add to BYL reaction, check by JC-1 and freeze

FIG. 4 continued

CytOx activity (units/ml)

METHODS AND COMPOSITIONS FOR CELL-FREE BIOLOGICAL REACTIONS

CROSS-REFERENCE TO RELATED APPLICATIONS

This application is a U.S. National Phase application under 35 U.S.C. 371 of International Application No. PCT/US2020/021763, filed Mar. 9, 2020, which claims priority to and the benefit of U.S. Provisional Application No. 62/815,445 filed Mar. 8, 2019, each of which is incorporated herein by reference in their entireties.

STATEMENT OF GOVERNMENT INTEREST

This invention was made with government support under grant number 1R43HG009988-01 awarded by the U.S. National Institutes of Health (NIH) and DE-SC0019827 awarded by the U.S. Department of Energy (DOE). The government has certain rights in the invention.

FIELD

Compositions and methods disclosed herein relate to improved in vitro cell-free systems.

BACKGROUND

There is extensive biological data encoded in DNA that is of unknown function. This data varies from naturally derived proteins, peptides, and molecular control components to semi-synthetic and engineered variants thereof. With the advent of high-throughput sequencing, as of 2017, more than 2.7 trillion bases of information are known, and only a small fraction are expressed. Tools that are able to determine the products of this DNA will be essential to understanding this information.

Separately, synthetic biology has emerged as an important field for which essential processes can be understood and engineered. Within this field there are both natural, semi-synthetic, and engineered genes, regulatory parts, and other components that are in need of testing.

Despite efforts and progresses, current approaches are limited to conduct high-throughput functional genomics to determine products from DNA and to promote synthetic biology approaches. Challenges still remain in developing engineering-driven approaches and systems to accelerate the design-build-test cycles required for reprogramming existing biological systems, constructing new biological systems and testing genetic circuits for transformative future applications in diverse areas including biology, engineering, green chemistry, agriculture and medicine.

An in vitro transcription-translation (TXTL) system (Shin & Noireaux 2012; Sun et al. 2013) has been developed which allows for the rapid prototyping of genetic constructs (Sun et al. 2014) in an environment that behaves similarly to a cell (Niederholtmeyer et al. 2015; Takahashi et al. 2015). One of the main purposes of working in vitro is to be able to generate fast speeds—in vitro, reactions can take 8 hours and can scale to thousands of reactions a day, a multi-fold improvement over similar reactions in cells (Sun et al. 2014).

However, in order to fully realize the potential for scaling TXTL systems, there is a need for improved TXTL systems, in particular for the purpose of protein production and enzymatic reactions.

SUMMARY

In one aspect, provided herein is a composition for in vitro TXTL, comprising: a cell-free extract derived from an organism; a nucleic acid; and an organelle that is heterologous to the organism.

In some embodiments, the organism is a prokaryotic organism including bacteria and/or archaea, preferably a bacterial cell such as E. coli. In certain embodiments, the organism comprises a eukaryotic organism such as a plant and/or animal. In some embodiments, the organism can be selected from: HeLa, CHO, carrots, insects, wheat germ, primary cancer cell line, primary cell line, leukocytes, eukaryota, plants, animals, archaea, Escherichia spp., Streptomyces spp., Actinobacteria, Bacillus spp., Vibrio spp., Rhodococcus spp., Clostridium spp., bacteria and any combination of the foregoing; wherein preferably the organism is selected from: HeLa, CHO, Bacillus, Pichia, wheat germ, carrot, and S. frugiperda insect cell. In some embodiments, the extract can be provided at a concentration of about 0.005-1000 mg/ml, 0.05-500 mg/ml, 0.5-100 mg/ml or 1-20 mg/ml, wherein preferably the extract has been at least partially purified.

In some embodiments, the nucleic acid comprises a linear DNA or a plasmid DNA or an RNA. In some embodiments, the nucleic acid comprises a template nucleic acid for expression into a desired RNA or protein product.

In some embodiments, the organelle can include intact organelle and/or non-intact organelle, wherein in the non-intact organelle, an outer membrane and/or inner membrane of the organelle have been at least partially disrupted. In some embodiments, the organelle is selected from the group consisting of: mitochondria, chloroplasts, bacterial carboxysomes, and any combination of one or more of the foregoing. In some embodiments, the organelle comprises mitochondria. In some embodiments, the organelle is present at a concentration of about 0.000015-100 mg/ml, 0.00015-50 mg/ml, 0.0015-10 mg/ml, or 0.15-4.5 mg/ml. In some embodiments, a ratio of the extract to the organelle is between about 100,000,000:1 and 0.00005:1; 600,000:1 and 0.005:1; 300:1 and 0.05:1; or 10:1 and 0.2:1, by weight (e.g., based on the amount of proteins and other components). In some embodiments, the organelle is at least partially purified. The organelle can be stored in a solution free of inhibitors to cell-free transcription and translation. In some embodiments, the organelle is derived from eukaryotic cells such as plant cells and/or animal cells.

In some embodiments, the composition further includes cofactors, enzymes, and other reagents for transcription and/or translation. In some embodiments, the composition can further include a substrate capable of entering the TCA cycle.

Another aspect relates to a method for protein production, comprising: providing any one of the compositions disclosed herein; expressing a protein from the nucleic acid in vitro in the composition; and isolating the protein from the composition.

A further aspect related to a composition for producing a desired product, comprising: a substrate; an enzyme that catalyzes a reaction of the substrate into a desired product; and an organelle derived from a first organism; wherein the composition is a cell-free composition for in vitro, catalytic reaction of the substrate into the desired product.

In some embodiments, the first organism is selected from eukaryotic cells such as plant cells and/or animal cells. In some embodiments, the composition can further include an extract derived from a second organism, wherein the organelle is heterologous to the second organism. In some embodiments, the second organism is selected from: HeLa, CHO, carrots, insects, wheat germ, primary cancer cell line, primary cell line, leukocytes, eukaryota, plants, animals, archaea, *Escherichia* spp., *Streptomyces* spp., Actinobacteria, *Bacillus* spp., *Vibrio* spp., *Rhodococcus* spp., *Clostridium* spp., bacteria and any combination of the foregoing; wherein preferably the second organism is selected from: HeLa, CHO, *Bacillus, Pichia,* wheat germ, carrot, and *S. frugiperda* insect cell.

Also provided herein is a method for in vitro preparation of a product, comprising: providing the composition for producing a desired product; allowing the enzyme to catalyze the reaction of the substrate into the desired product; and isolating the desired product from the composition.

Kits for producing desired products (including protein products as well as small molecule products) are also provided, which can include some or all components of any one of the compositions disclosed herein. The kit can additionally include a pamphlet containing instruction of use.

BRIEF DESCRIPTION OF THE DRAWINGS

FIG. 3 outlines the preparation of Tobacco cell extracts.

FIG. 4 outlines the preparation of plant mitochondria.

Figure 1:
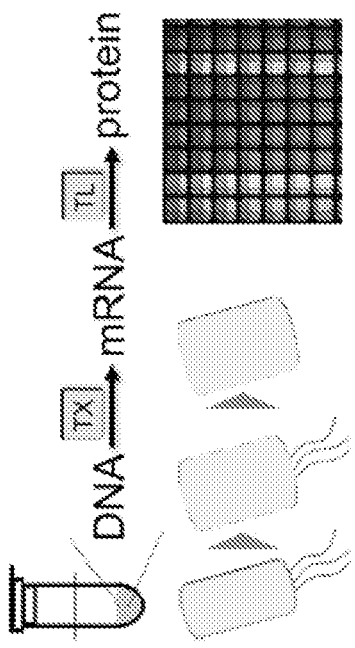
FIG. 1 provides an overview of cell-free expression. In cell-free expression, a host is converted into a lysate and supplied with factors to enable the conversion of DNA to mRNA and protein.

While the above-identified drawings set forth presently disclosed embodiments, other embodiments are also contemplated, as noted in the discussion. This disclosure presents illustrative embodiments by way of representation and not limitation. Numerous other modifications and embodiments can be devised by those skilled in the art which fall within the scope and spirit of the principles of the presently disclosed embodiments.

DETAILED DESCRIPTION

Disclosed herein are compositions and formulations for various biological reactions such as protein production and enzymatic reactions in cell-free systems (also termed "anaerobic in vitro systems"), and methods of using the same. In some embodiments, the system can be cell-free transcription and translation (TXTL) systems. For example, a cell-free TXTL system can include: an extract derived from one or more organisms; a nucleic acid; and one or more heterologous organelles. The compositions may also include separate energy recycling systems for providing phosphate potential or redox potential. In an embodiment, cell-free TXTL systems described herein can include: a first set of cofactors, enzymes, and other reagents necessary for transcription and/or translation; a second set of cofactors, enzymes, and other reagents necessary for energy recycling; a template nucleic acid comprising a gene or gene portion of interest; and one or more heterologous organelles.

In certain embodiments, the system can be designed for various enzymatic reactions. Such systems can include: one or more substrates; one or more enzymes that catalyze a reaction of the one or more substrates; and one or more heterologous organelles.

Without wishing to be bound by theory, it is believed that the systems disclosed herein are advantageous over conventional systems, at least because they can efficiently maintain homeostasis of cell-free systems. This is critical, as it is often difficult to isolate specific cofactors or imbalances in a system, especially as the system is dynamically changing depending on inputs and surroundings. By providing organelles into the system, homeostasis can be dynamically maintained, thereby unlocking the full versatility of the in vitro system. Particularly, the balance of cofactors, such as ATP (ADP/AMP), NADPH(NADP+), NADH(NAD+), can be maintained throughout the system. Maintenance of homeostasis can lead to longer cell-free expression times, thereby maximizing the amount of product formed and expression conditions.

An estimated 70 components participate in the mechanism of transcription and translation in *E. coli*. Exergonic metabolic pathways supply energy currency to drive the endergonic reactions of gene expression in the form of phosphate potential ([ATP]/[ADP]+[Pi]), and redox potential ([NAD(P)H]/[NAD(P+)]). The number, identities, specificities and mechanisms of expression system components can vary across phyla and reflect evolution under environmentally select conditions.

While methods exist to maintain cofactor homeostasis, such as ATP regeneration through exogenous systems such as PEP/CK, Cytomim, or CP/CK, these methods are still limiting in the reaction volumes that can be maintained. Additionally, these methods require definition of the cofactor itself and the metabolism and catabolism of the cofactor, for which in a lysate may be difficult.

Disclosed herein are methods for providing cell-free reactions with "factories" that can conduct cofactor regeneration and balance. In the same way that a cell is able to maintain its physiological state through homeostatic biochemical mechanisms, cell-free reactions can be engineered to endogenously self-regulate. This system improves upon prior systems by providing dynamic control of the cell-free expression system. This can extend reaction times and open up new application spaces. When used for biodiscovery, the compositions and methods disclosed herein can remove largely unsolved barriers to conventional gene expression in heterologous hosts, opening vast areas of gene sequence space for exploration; via expression of genes from uncultured organisms, microbiomes, libraries of cryptic genes and clusters.

In some embodiments, it has been surprisingly discovered that the transfer of organelles from one species to another species, or "heterologous" organelles, enables higher cell-free expression yields and/or rates. Organelles are highly evolved from one organism to another. For example, with few exceptions only organisms from the domain eukarya contain mitochondria and chloroplasts. *Nicotiana tabacum* (Tobacco) cv. BY-2, and *Escherichia coli* are extremely phylogenetically apart from each other—they belong to different domains, let along genus and species. Therefore, it is extremely surprising that when supplementing mitochondria from, e.g., Tobacco into cell-free lysates from a different species, e.g., *Escherichia coli*, the mitochondria still increase cell-free expression yields and/or rates. This implies that the mitochondria present from a very distant organism are able to interact with the biochemistry of another distant organism and provide a positive effect. It is also surprising that supplementing organelles from different domains, kingdoms, phylums, classes, orders, families, genus, or species in between one another can provide a positive effect, as the organelle is highly evolved. This includes positive effects on cell-free expression yields and/or rates from supplementation of a mammalian (e.g., (*Homo sapiens*)) cell-free expression system with plant (e.g., Tobacco) mitochondria, as Tobacco comes from the plantae kingdom and humans from the animalia kingdom. In addition, supplementation of a Hela cell-free expression system with Tobacco chloroplasts is further unexpected given that *H. sapiens* do not natively have chloroplasts.

Definitions

For convenience, certain terms employed in the specification, examples, and appended claims are collected here. Unless defined otherwise, all technical and scientific terms used herein have the same meaning as commonly understood by one of ordinary skill in the art to which this disclosure belongs.

The articles "a" and "an" are used herein to refer to one or to more than one (i.e., at least one) of the grammatical object of the article. By way of example, "an element" means one element or more than one element.

As used herein, the term "about" means within 20%, more preferably within 10% and most preferably within 5%. The term "substantially" means more than 50%, preferably more than 80%, and most preferably more than 90% or 95%.

As used herein, "a plurality of" means more than 1, e.g., 2, 3, 4, 5, 6, 7, 8, 9, 10, 11, 12, 13, 14, 15, 16, 17, 18, 19, 20, or more, e.g., 25, 30, 40, 50, 60, 70, 80, 90, 100, 200, 300, 400, 500, or more, or any integer therebetween.

The term "additive" refers to an addition, whether chemical or biological in nature, whether natural or synthetic or, that is provided to a system. Examples include but are not limited to enzymes, oxidases, oxygenases, sugars, betaine, cyclodextrans, solvents, alcohols, proteins, enzymes, nucleic acids, organelles, mitochondria, and chloroplasts.

As used herein, the terms "nucleic acid," "nucleic acid molecule" and "polynucleotide" may be used interchangeably and include both single-stranded (ss) and double-stranded (ds) RNA, DNA and RNA:DNA hybrids. These terms are intended to include, but are not limited to, a polymeric form of nucleotides that may have various lengths, including deoxyribonucleotides and/or ribonucleotides, or analogs or modifications thereof. A nucleic acid molecule may encode a full-length polypeptide or RNA or a fragment of any length thereof, or may be non-coding.

Nucleic acids can be naturally-occurring or synthetic polymeric forms of nucleotides. The nucleic acid molecules of the present disclosure can be formed from naturally-occurring nucleotides, for example forming deoxyribonucleic acid (DNA) or ribonucleic acid (RNA) molecules. Alternatively, the naturally-occurring oligonucleotides can include structural modifications to alter their properties, such as in peptide nucleic acids (PNA) or in locked nucleic acids (LNA). The terms should be understood to include equivalents, analogs of either RNA or DNA made from nucleotide analogs and as applicable to the embodiment being described, single-stranded or double-stranded polynucleotides. Nucleotides useful in the disclosure include, for example, naturally-occurring nucleotides (for example, ribonucleotides or deoxyribonucleotides), or natural or synthetic modifications of nucleotides, or artificial bases. Modifications can also include phosphorothioated bases for increased stability.

As used herein, unless otherwise stated, the term "transcription" refers to the synthesis of RNA from a DNA template; the term "translation" refers to the synthesis of a polypeptide from an mRNA template. Translation in general is regulated by the sequence and structure of the 5' untranslated region (5'-UTR) of the mRNA transcript. One regulatory sequence is the ribosome binding site (RBS), which promotes efficient and accurate translation of mRNA. The prokaryotic RBS is the Shine-Dalgarno sequence, a purine-rich sequence of 5'-UTR that is complementary to the UCCU core sequence of the 3'-end of 16S rRNA (located within the 30S small ribosomal subunit). Various Shine-Dalgarno sequences have been found in prokaryotic mRNAs and generally lie about 10 nucleotides upstream from the AUG start codon. Activity of a RBS can be influenced by the length and nucleotide composition of the spacer separating the RBS and the initiator AUG. In eukaryotes, the Kozak sequence lies within a short 5' untranslated region and directs translation of mRNA. An mRNA lacking the Kozak consensus sequence can also be translated efficiently in an in vitro system if it possesses a moderately long 5'-UTR that lacks stable secondary structure. While *E. coli* ribosome preferentially recognizes the Shine-Dalgarno sequence, eukaryotic ribosomes (such as those found in retic lysate) use the Kozak ribosomal binding site.

As used herein, the term "host" or "host cell" refers to any prokaryotic or eukaryotic single cell (e.g., yeast, bacterial, archaeal, etc.) cell or organism. The host cell can be a recipient of a replicable expression vector, cloning vector or any heterologous nucleic acid molecule. Host cells can be prokaryotic cells such as species of the genus *Escherichia* or *Lactobacillus*, or eukaryotic single cell organism such as yeast. The heterologous nucleic acid molecule can contain, but is not limited to, a sequence of interest, a transcriptional regulatory sequence (such as a promoter, enhancer, repressor, and the like) and/or an origin of replication. As used herein, the terms "host," "host cell," "recombinant host" and "recombinant host cell" can be used interchangeably. For examples of such hosts, see Green & Sambrook, 2012, Molecular Cloning: A laboratory manual, 4th ed., Cold Spring Harbor Laboratory Press, New York, which are hereby incorporated by reference herein in their entireties.

The term "archaea" or "domain Archaea" refer to any of a group of single-celled prokaryotic organisms (that is, organisms whose cells lack a defined nucleus) that have distinct molecular characteristics separating them from bacteria as well as from eukaryotes (organisms, including plants and animals, whose cells contain a defined nucleus). Members of the archaea include: *Pyrolobus fumarii*, which holds the upper temperature limit for life at 113° C. (235° F.) and was found living in hydrothermal vents; species of *Picrophilus*, which were isolated from acidic soils in Japan and are the most acid-tolerant organisms known—capable of growth at around pH 0; and the methanogens, which produce methane gas as a metabolic by-product and are found in anaerobic environments, such as in marshes, hot springs, and the guts of animals, including humans.

As used herein, the term "selectable marker" or "reporter" refers to a gene, operon, or protein that upon expression in a host cell or organism, can confer certain characteristics that can be relatively easily selected, identified and/or measured. Reporter genes are often used as an indication of whether a certain gene has been introduced into or expressed in the host cell or organism. Examples, without limitation, of commonly used reporters include: antibiotic resistance ("abR") genes, fluorescent proteins, auxotropic selection modules, β-galactosidase (encoded by the bacterial gene lacZ), luciferase (from lightning bugs), chloramphenicol acetyltransferase (CAT; from bacteria), GUS (β-glucuronidase; commonly used in plants) green fluorescent protein (GFP; from jelly fish), and red fluorescent protein (RFP). Typically host cells expressing the selectable marker are protected from a selective agent that is toxic or inhibitory to cell growth.

The term "engineer," "engineering" or "engineered," as used herein, refers to genetic manipulation or modification of biomolecules such as DNA, RNA and/or protein, or like technique commonly known in the biotechnology art.

As described herein, "genetic module" and "genetic element" may be used interchangeably and refer to any coding and/or non-coding nucleic acid sequence. Genetic modules may be operons, genes, gene fragments, promoters, exons, introns, regulatory sequences, tags, or any combination thereof. In some embodiments, a genetic module refers to one or more of coding sequence, promoter, terminator, untranslated region, ribosome binding site, polyadenylation tail, leader, signal sequence, vector and any combination of the foregoing. In certain embodiments, a genetic module can be a transcription unit as defined herein.

As used herein, a "homolog" of a gene or protein, "homology," or "homologous" refers to its functional equivalent in another species. The terms "substantial identity" in the context of a peptide indicates that a peptide comprises a sequence with at least 70% sequence identity to a reference sequence, for example at least 80%, at least 85%, at least 90%, at least 95%, at least 96%, at least 97%, at least 98%, or at least 99% sequence identity to the reference sequence, over a specified comparison window. Optionally, optimal alignment is conducted using the homology alignment algorithm of Needleman and Wunsch, J. Mol. Biol. 48:443 (1970). An indication that two peptide sequences are substantially identical is that one peptide is immunologically reactive with antibodies raised against the second peptide. Thus, a peptide is substantially identical to a second peptide, for example, where the two peptides differ only by a conservative substitution. Peptides which are "substantially similar" share sequences as noted above except that residue positions that are not identical may differ by conservative amino acid changes.

As used herein, a "variant" of a gene or nucleic acid sequence is a sequence having at least 10% identity with the referenced gene or nucleic acid sequence, and can include one or more base deletions, additions, or substitutions with respect to the referenced sequence. The differences in the sequences may by the result of changes, either naturally or by design, in sequence or structure. Natural changes may arise during the course of normal replication or duplication in nature of the particular nucleic acid sequence. Designed changes may be specifically designed and introduced into the sequence for specific purposes. Such specific changes may be made in vitro using a variety of mutagenesis techniques. Such sequence variants generated specifically may be referred to as "mutants" of the original sequence. A "variant" of a peptide or protein is a peptide or protein sequence that varies at one or more amino acid positions with respect to the reference peptide or protein. A variant can be a naturally-occurring variant or can be the result of spontaneous, induced, or genetically engineered mutation(s) to the nucleic acid molecule encoding the variant peptide or protein. A variant peptide can also be a chemically synthesized variant.

As used herein, the term "organelle" refers to a specialized subunit within a cell that has a specific function, and is separately enclosed within its own lipid membrane. Accordingly, the types of organelles may include nuclei, mitochondria, endoplasmic reticulum, Golgi apparati, vacuoles, lysosomes, peroxisomes, chloroplasts, acrosomes, autophagosomes, centrioles, ciliums, glycosomes, glyoxysomes, hydrogenosomes, melanosomes, mitosomes, myofibrils, nucleoli, parenthesomes, peroxisomes, ribosomes, or vesicles. The term "organelle" also encompasses other subcellular components including plasma membranes, flagellum, cilium, cell walls, cytoskeleton, and plasmodesmata. In a typical embodiment, the types of organelles include nuclei, mitochondria, endoplasmic reticulum, Golgi apparati, vacuoles, lysosomes, plasma membranes, or peroxisomes.

As used herein, the term "heterologous" means, when used in the context of organelles and cell-free extracts, such organelles that are derived from another organism and do not naturally exist in the same cell or organism from which the cell-free extracts are derived.

As used herein, "cofactors" are compounds involved in biochemical reactions that are recycled within the cells and remain at approximately steady state levels. Common examples of cofactors involved in anaerobic fermentation include, but are not limited to, $NAD^+$ and $NADP^+$ and ADP. In metabolism, a cofactor can act in oxidation-reduction reactions to accept or donate electrons. When organic compounds are broken down by oxidation in metabolism, their energy can be transferred to $NAD^+$ by its reduction to NADH, to $NADP^+$ by its reduction to NADPH, or to another cofactor, $FAD^+$, by its reduction to FAD¾. The reduced cofactors can then be used as a substrate for a reductase.

As used herein, the term "homeostasis", and derivatives thereof, refers to the ability to regulate variables such that conditions remain stable and relatively constant. This includes physiological processes and biological mechanisms and pathways involved in the maintenance of an internal metabolic equilibrium or steady-state of substrates within a cell-free system. For instance, when ATP and ADP levels are at homeostasis, the levels are within a balance that permits continued cell-free expression (at a ratio above 0.8), and maintained in that range.

Other terms used in the fields of recombinant nucleic acid technology and molecular and cell biology as used herein will be generally understood by one of ordinary skill in the applicable arts.

Cell-Free Compositions

The in vitro transcription and translation system is a system that is able to conduct transcription and translation outside of the context of a cell. In some embodiments, this system is also referred to as "cell-free system", "cell-free transcription and translation", "TXTL", "TXTL", "TX/TL", "extract systems", "in vitro system", "ITT", or "artificial cells." Exemplary in vitro transcription and translation systems include purified or partially purified protein systems that are made from hosts, purified or partially purified protein systems that are not made from hosts, and protein systems made from a host strain that is formed as an "extract". In an embodiment, extracts include whole-cell extracts, nuclear extracts, cytoplasmic extracts, combinations thereof, and the like. Whole-cell extracts are also termed lysates herein. Lysates, and lysate systems, described herein, are intended to be non-limiting examples of extracts; where lysate is described herein, it is contemplated that other extracts, or extracts and protein combinations, can be used.

In an embodiment, a cell-free system can include a combination of cytoplasmic and/or nuclear components from cells. The components can include extracts, purified components, or combinations thereof. The extracts, purified components, or combinations thereof include reactants for protein synthesis, transcription, translation, DNA replication and/or additional biological reactions occurring in a cellular environment identifiable by a person skilled in the art.

Figure 2:
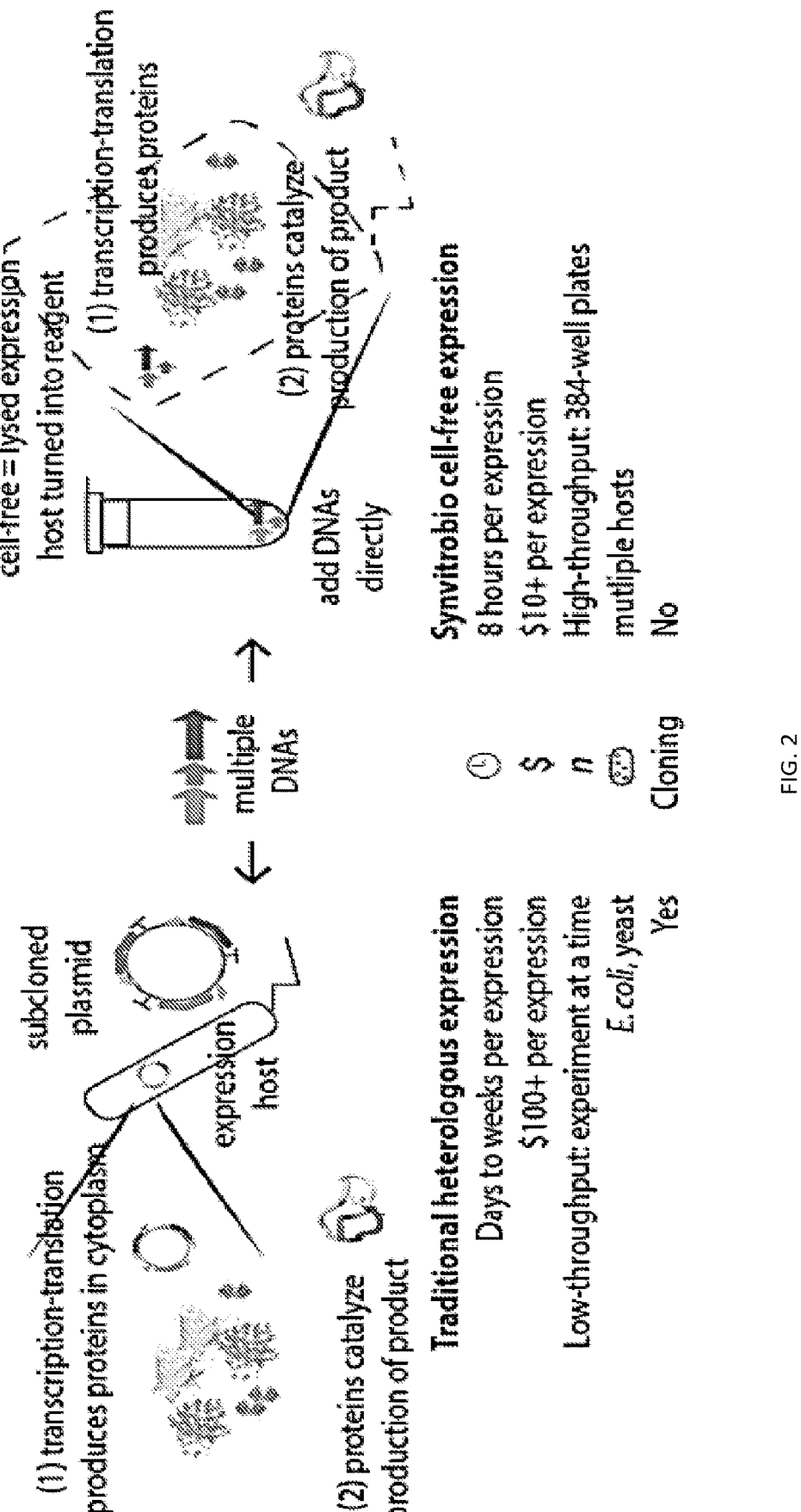
FIG. 2 provides a comparison of traditional heterologous expression to cell-free expression.

Cell-free transcription-translation is described in FIG. 1. Top, cell-free expression that takes in DNA and produces protein that catalyzes reactions. Bottom, diagram of cell-free production and representative data collected in 384-well plate format of GFP expression. Cell-free approaches contrasted to cellular approaches are described in FIG. 2. Cell-free platform allows for protein expression from multiple genes without live cells. Cell-free production biotechnology methods produce lysates from prokaryotic cells that are able to take recombinant DNA as input and conduct coupled transcription and translation to output enzymatically active protein. Cell-free systems take only 8 hours to express, rather than days to weeks in cells, since there is no need for cloning and transformation. They are also at least 10-fold cheaper to run than cells, and can be run in high-throughput as reactions are the equivalent of a reagent and used in a 384-well plate. Typical yields of prokaryotic systems are 750 µg/mL of GFP (30 µM). Cell-free systems can multiple organisms can be implemented and expression conducted at scales from 10 µl up to 10 mL.

Directions on how to make the extract component of cell-free systems, particularly lysates from *E. coli*, can be found in (Sun et al. 2013), which is hereby incorporated by reference herein in its entirety; other methods for producing a lysate are known to one of ordinary skill in the art. While this procedure is adapted for *E. coli* cell-free systems, it can be used to produce other cell-free systems from other organisms and hosts (prokaryotic, eukaryotic, archaea, fungal, etc.) Examples, without limitation, of the production of other cell-free systems include *Streptomyces* spp. (Thompson et al. 1984), *Bacillus* spp. (Kelwick et al. 2016), and Tobacco BY2 (Buntru et al. 2014), which are hereby incorporated herein by reference in their entireties. Exemplary processes for producing lysates involve growing a host in a rich media to mid-log phase, followed by washes, lysis by French Press and/or Bead Beating Homogenization and/or equivalent method, and clarification. A lysate that has been processed as such can be referred to as a "lysate", or a "treated cell lysate", and is a non-limiting example of an "extract". In an embodiment, cells can be grown under anaerobic conditions. In an aspect, an extract can be prepared under anaerobic conditions.

One or more additives can be supplied along-side an extract to maintain gene expression. Contemplated additives include those tailored to replicate the in vivo expression and/or the metabolic environment of the lysate source organism, e.g., redox buffering agents, phosphate potential buffering agents, customized energy regeneration systems, native ribosomes, chaperones, species-specific tRNAs, pH buffering, metals (such as Magnesium and Potassium), osmoregulatory agents, gas concentrations; [O2], [CO2], [N2], sugars, maltose, starch, maltodextrin, glucose, glucose-6-phosphate, fructose-1,6-biphosphate, 3-phospho-glycerate, phosphoenolpyruvate, pyruvate kinase, pyruvate dehydrogenase, pyruvate, acetyl phosphate, acetate kinase, creatine kinase, creatine phosphate, glutamate, amino acids, ATP, GTP, CTP, UTP, ADP, GDP, CDP, UDP, AMP, GMP, CMP, UMP, folinic acid, spermidine, putrescine, betaine, DTT, TCEP, b-mercaptoethanol, TPP, FAD, FADH, NAD, NADH, NADP, NADPH, oxalic acid, CoA, glutamate-salts, acetate-salts, cAMP, native polymerases, synthetic polymerases, phage polymerases, temperature regulation conditions. A review of optional additives can be found in (Chiao et al. 2016), which is hereby incorporated by reference herein in its entirety. Optional additives can also include components that assist transcription and translation, such as phage polymerases, T7 RNA polymerase (RNAP), SP6 phage polymerase, cofactors, elongation factors, nanodiscs, vesicles, and antifoaming agents. Optional additives can also include additives to protect DNA, such as, without limitation, gamS, Ku, junk DNA, DNA mimicry proteins, chi site-DNA, or other DNA protective agents.

In some embodiments, the reaction can include more than 0.1% (w/v) of crowding agent. Macromolecular crowding refers to the effects of adding macromolecules to a solution, as compared to a solution containing no macromolecules. Such macromolecules are termed crowding agents. A contemplated crowding agent can be from a single source, or can be a mix of different sources. The crowding agent can be from varied sizes. In some embodiments, the crowding agents include polyethylene glycol and its derivatives, polyethylene oxide or polyoxyethylene.

An energy recycling and/or regeneration system drives synthesis of mRNA and proteins by providing ATP to a system and by maintaining system homeostasis by recycling ADP to ATP, by maintaining pH, and generally supporting a system for transcription and translation. A review of energy recycling systems can be found in (Chiao et al. 2016), which is hereby incorporated by reference herein in its entirety. Examples, without limitation, of energy recycling and/or systems that can be used include Glycerate 3-phosphate (3-PGA) (Sun et al. 2013), creatinine phosphate/creatinine kinase (CP/CK) (Kigawa et al. 1999), PANOx (Kim & Swartz 2001), and glutamate (Jewett & Swartz 2004). Other recycling and/or systems include those that can regenerate redox potential ([NAD(P)H]/[NAD(P+)]). An example of redox recycling is described in (Opgenorth et al. 2014). Recycling and/or systems can utilize innate central metabolism pathways from the host (for example, glycolysis, oxidative phosphorylation), externally supplied metabolic pathways, or both.

The in vitro transcription and translation system includes one or more nucleic acids. In an embodiment, the nucleic acid can include DNA, RNA, or combinations thereof. In some embodiments, a DNA can be supplied that that can produce a protein by utilizing transcription and translation machinery in the extract and/or additions to the extract. This DNA can have regulatory regions, such as under the OR2-OR1-Pr promoter (Sun et al. 2013), the T7 promoter or T7-lacO promoter, along with a RBS region, such as the UTR1 from lambda phage. The DNA can be linear or plasmid. In some embodiments, gene sequences can be engineered for cell-free expression in TXTL systems derived from the lysate source organism, such as: 5' rare codons for improved TXTL coupling, 5' AT/GC content for improved TXTL coupling, UTR, RBS, termination sequences, 5' fusions for improved TXTL coupling, gene fusions for improved TXTL coupling, fusions for protein stability, sequence deletions to promote solubility of membrane proteins, and protein tags.

In other embodiments, a mRNA can be supplied that utilizes translational components in the lysate and/or additions to the lysate to produce a protein. The mRNA can be from a purified natural source, or from a synthetically generated source, or can be generated in vitro, e.g., from an in-vitro transcription kit such as HiScribe™, MAXIscript™, MEGAscript™, mMESSAGE MACHINE™, MEGAshort-script™.

In some embodiments, non-canonical amino acids can be utilized in the composition. Non-canonical amino acids can be found naturally in the cellular-produced product, or can be artificially added to the product to produce desirable properties, such as tagging, visualization, resistance to degradation, or targeting. While implementation of non-canonical amino acids is difficult in cells, in cell-free systems implementation rates are higher due to the ability to saturate with the non-canonical amino acid. Examples, without limitation, of non-canonical amino acids, including ornithine, norleucine, homoarginine, tryptophan analogs, biphenylalanine, hydrolysine, pyrrolysine, or as described in (Blask-ovich 2016) which is hereby incorporated by reference herein in its entirety.

In some embodiments, the input nucleic acids are derived from extremophiles or anaerobes. The composition can produce the desired product using these environmental sequences by emulating the activity of the host cell (e.g., in producing an anaerobic environment), thereby acting as an "artificial cell" or an alternate heterologous expression platform.

Organelles

In some embodiments, organelles can be added to the cell-free system. In certain embodiments, the added organelles can help maintain homeostasis. The organelles can be supplied exogenously and/or from a heterologous source to the cell-free system to supplement the system as an additive.

In some embodiments, the activity of the organelle is to enable the recycling of enzymatic cofactors and/or substrates. As the cell-free system progresses, the organelle dynamically responds to cofactor and/or substrate imbalance in the cell-free system and regenerates cofactors and/or substrate to produce balance. For example, if an ATP to ADP ratio is not ideal for expression, the organelle will rebalance the ratio to maintain optimal homeostasis states. The activity of the organelle mirrors its activity in its native environment (e.g., where it is sourced).

In some embodiments, the organelles specifically maintain cofactor balance, ATP(ADP/AMP), NADPH(NADP+), NADH(NAD+), and/or GTP(GDP/GMP). These cofactors are known to be important for the progression of cell-free expression and for the formation of certain products in the cell-free system.

In some embodiments, the organelles maintain redox potential of the cell-free system. Redox potential can be further modified by the addition of substrates that are reducing or oxidizing, such as DTT or TCEP. This can assist in production of different products.

In some embodiments, the organelles extend reaction duration of the cell-free system. The organelles do so by extending the duration in which cofactor and/or substrate ratios do not enter a toxic regime.

The organelles are provided exogenously to the cell-free reaction, and do not need to be derived from the same organism as of the host cell-free reaction. In some embodiments, the organelles are added to systems that do not contain lysate (e.g., purified protein cell-free systems), and serve as purely maintaining homeostasis. In some embodiments, the organelle is exogenously purified and produced separately from the host cell-free system, and then added to the cell-free system independently.

In some embodiments, the organelle is a prokaryotic organism that is added into a cell-free system that is unable to divide and multiply (e.g., by providing a toxin that is bacteriostatic). In doing so, the prokaryotic organism provides homeostasis for the host, but is unable to digest the components of the cell-free system to promote its own growth.

In some embodiments, the organelle can be supplied to the reaction as a purified organelle. Purification can be achieved by centrifugation, filtration, or other purification and separation techniques known to one of ordinary skill in the art. Examples of separation include differential centrifugation or density gradient centrifugation. The purified organelle can be produced separately from the host cell-free system and stored in a buffer that allows for long-term storage. The buffer can include sucrose and other cryoprotectants. The organelles can be supplemented as purified components into cell-free systems, either in its original buffer if the buffer is compatible with cell-free expression or in another buffer that is compatible by dialysis or buffer transfer. The dose of the organelle can be titrated for optimal homeostasis maintenance. The presence of the organelle and its activity can be detected through staining and microscopy or through inspection of different components using antibodies and visualization methods (e.g., episilon subunit of tonoplast H+ ATPase, cell compartment antibody markers such as catalase, luminal binding-protein, isocitrate dehydrogenase, cytochrome oxidase subunit II, voltage-dependent anion-selective channel protein 1).

In some embodiments, the organelles can be supplied to the reaction in a crude form. This organelle form can be produced separately from the host cell-free system, or can be isolated during the production of the host cell-free system. Preferably, the organelle is isolated as a crude cellular lysate that can then be titrated into the cell-free system. The crude cellular lysate can be devoid of inhibitory components that prevent cell-free expression, such as peroxisomes or vacuoles that can lead to protein, DNA, or mRNA degradation.

In some embodiments, the organelles are derived from different organisms. These include plants, animals, or single-celled organisms of the eukaryote and/or from bacteria. Different organelles can be more effective with different cell-free systems. Without wishing to be bound by theory, it has been hypothesized that the fidelity and yield of in vitro gene expression will be optimal within the context of a phylogenetically similar TXTL system with genes or organelles engineered for optimum expression.

In some embodiments, the organelles have outer cell walls. This is a property frequently associated with organelles from plant systems. Outer cell walls can allow for higher stability of the organelle, both during storage and during addition to a cell-free system. In some embodiments, the organelles can survive freeze-thaw cycles for long-term storage. The is also a property associated with organelles from systems that natively survive freeze-thaw cycles, such as plants. In some embodiments, the organelles are derived from plant cell lines (e.g., carrot, tobacco, wheat germ, etc.).

In some embodiments, the organelles are selected from mitochondria and/or chloroplasts and/or bacterial carboxysomes. Specifically, mitochondria are capable of conducting the TCA (tricarboxylic acid) cycle and generating ATP, but will require an energy source and a supply of molecular oxygen. Chloroplasts are able to conduct carbon fixation, and will require a supply of carbon dioxide (which can be atmospheric) as well as a light source. These can be further supplemented with an energy source that can also be metabolized.

In some embodiments, the composition can include a substrate capable of entering the TCA cycle—a series of chemical reactions used by all aerobic organisms to release stored energy through the oxidation of acetyl-CoA derived from carbohydrates, fats, and proteins, into adenosine triphosphate (ATP) and carbon dioxide. The substrate can directly or indirectly enter the TCA cycle. Commonly used substrates include glutamine, glutamate, succinate, and malate, without limitation. In a preferred embodiment, glutamate, either in purified form or as part of a salt complex (e.g., Magnesium, Potassium) can be added to the reaction at concentrations of 0.01 mM to 10 M, preferentially 0.1 mM to 1 M, more preferentially 1 mM-500 mM.

In some embodiments, the cell-free systems include purified enzymes where enzymes are combined together to produce a product, either from an exogenously supplied input or from the enzymes themselves. These in vitro compositions do not have to conduct transcription and/or translation to produce products, with an exemplary example, without limitation, described in (Opgenorth et al. 2014), which is hereby incorporated by reference herein in its entirety. Examples in the literature, without limitation, include the conversion of glucose and/or other sugars to bioplastics, terpenoid-like molecules (isoprene, limonene), to hydrogen, to tagatose, and to allulose. Purified enzymes, added together with an energy and/or redox potential regeneration system, can convert inputs to outputs at high concentrations (mg/mL). For many of these reactions, the enzymes involved or the substrates can require homeostasis to function properly or to produce economically viable yields.

In some embodiments, the cell-free enzymatic systems include combinations of lysates derived from one or more natural or engineered organisms that are mixed together to produce a product, either from an exogenously supplied input or from the components of the lysates themselves. Within each lysate, a necessary enzyme or pathway can be overproduced by genetic engineering methods. An example, without limitation, is described as "cell-free metabolic engineering" in (Opgenorth et al. 2014; Karim & Jewett 2016), which are hereby incorporated by reference herein in their entireties. Further, in some embodiments, the in vitro compositions are combinations of both lysates and purified enzymes. These are supplemented with organelles to provide homeostasis.

In some embodiments, heterologous organelles such as mitochondria or chloroplasts can be added to eukaryotic cell-free systems to improve cell-free expression and/or in vitro enzymatic reactions (e.g., increased rate, sustained reaction, etc.). Even within the kingdom animalia, there is significant genetic variation between different eukaryotes, but the addition of heterologous organelles is still beneficial. This can be applied to the production of various proteins, specifically proteins of therapeutic interest such as antibodies, T-cell receptors, drug targets, antigens, and others for which production in a mammalian (e.g., HeLa) cell-free system can provide distinct advantages (e.g. post-translational modifications such as glycosylation, disulfide bridge maintenance) but that are limited by the yields of current HeLa cell-free systems without heterologous organelle addition. In addition, the method described herein (e.g., Example 8) does not only apply to HeLa cell-free systems, but can also apply to other cell-free systems, such as CHO, Sf9, Sf21, carrot, and other systems from eukaryotic origin.

In some embodiments, organelles provided can be either completely intact, partially intact, or not intact. The amount of intact organelle can be determined visually by light or electron microscopy. For microscopy, the organelle can be pre-stained with colorimetric solutions or fluorescent solutions to aid in visualization. In addition, to indirectly determine the amount of certain types of intact organelles, such as mitochondria, activity assays can be used. For example, cytochrome c oxidase activity can be measured as a proxy for outer membrane integrity. Cytochrome c oxidase is normally on the inner mitochondrial membrane, but in disrupted mitochondria where the outside membrane is damaged or in mitochondria treated with detergents (eg n-Dodecyl beta D-maltoside, or DDM) the oxidation of ferricytochrome c can be measured. The ratio: (cytochrome C oxidase activity w/DDM–cytochrome C oxidase activity w/o DDM)*100/(cytochrome C oxidase activity w/DDM) can then be measured to determine percent mitochondria with undamaged outer membranes. Indirect assays can also be used to measure intact chloroplasts, such as measuring the fixation of carbon dioxide into photosynthetic products.

Partially intact or not intact mitochondria are also potentially capable of increasing cell-free expression rates and/or yields. While surprising, because the resulting composition of disrupted mitochondria still maintain the components within the mitochondria, the resulting solution may be able to sill support cell-free expression rates and/or yields. Disrupted mitochondria in particular may still be capable of supporting oxidative phosphorylation in the context of a cell-free reaction.

Kits and Methods

Various methods for using the cell-free systems are provided herein. In some embodiments, the system can be used for protein synthesis or in vitro TXTL. The methods can include: providing a cell-free TXTL composition described herein, wherein the TXTL composition is designed to synthesize one or more proteins; and isolating the one or more proteins from the composition.

A further aspect relates to methods for in vitro preparation of a product that is the result of an enzymatic reaction. The methods include: providing a cell-free enzymatic reaction composition described herein, allowing the one or more enzymes to react with the substrates contained in the composition, so as to produce the product, and isolating the product from the composition. In some embodiments, the enzymes and their substrates can be selected to react and produce the desired products. The enzymes can be recombinantly prepared.

In an embodiment, a product can be made in vitro, where one or more substrates, one or more enzymes, and one or more heterologous organelles can be mixed together to produce a subsequent product and sustain long production periods. The one or more enzymes can react with the provided substrate to produce the desired product. In the course of producing the product, homeostatic balance can be achieved, such as maintenance and balance of ATP(ADP/AMP), NADPH(NADP+), NADH(NAD+), and/or GTP (GDP/GMP). Production periods of the product can be extended for multiple days to weeks. Critically, the addition of the heterologous organelles will help even in scenarios where transcription and translation is not occurring.

The product can be of various small molecules that are made from the action of enzymes, or from proteins that are made from the action of enzymes (such as a ribosomal synthesized and post-translationally modified peptide, where the input is a peptide sequence). In addition, other combinations of enzymes to maintain cofactor balance and additives can be utilized in the reaction. The presence of organelles such as mitochondria can regulate cofactor balance dynamically in instances where the reaction is either not balanced for or is poorly balanced over time, thereby increasing product formation and/or duration of product formation.

Kits are also provided herein which can include some or all components of the composition disclosed herein. An instruction manual can be provided in the kit for how to use it.

EXAMPLES

Example 1. Mitochondria Addition to Tobacco Cell-Free System

To test the addition of mitochondria to a Tobacco cell-free system, initially a Tobacco cell-free lysate was produced using the methods described in (Komoda et al. 2004), included without limitation, with modifications based on the outline in FIG. 3. Specifically, the protoplast wash buffer consisted of 12.5 mM NaOAc, 5 mM $CaCl_2$, 0.37 M Mannitol, pH 5.8 with acetic acid. The wash buffer has enzymes added to 3% (v/v) Rohament CL, 2% (v/v) Rohament PL, and 0.1% (v/v) Rohapect UF (AB Enzymes, Darmstadt, Germany). Percoll gradients were conducted at: 70%, 40%, 30%, 0% Percoll in 0.7 M mannitol—20 mM $MgCl_2$—5 mM PIPES-KOH (pH 7.0). Centrifugation was conducted at 10,000×g for 1 hour in a SW41 rotor at 25° C. Translation buffer consisted of: 30 mM HEPES-KOH pH 7.4—60 mM potassium glutamate—0.5 mM Mg glutamate—2 mM DTT], with 1 tablet of Complete Mini EDTA-free (Roche).

In addition, mitochondria were separated from Tobacco cells through methods described in (Meyer & Millar 2008), included without limitation, with modifications based on that outlined in FIG. 4.

Figure 5:
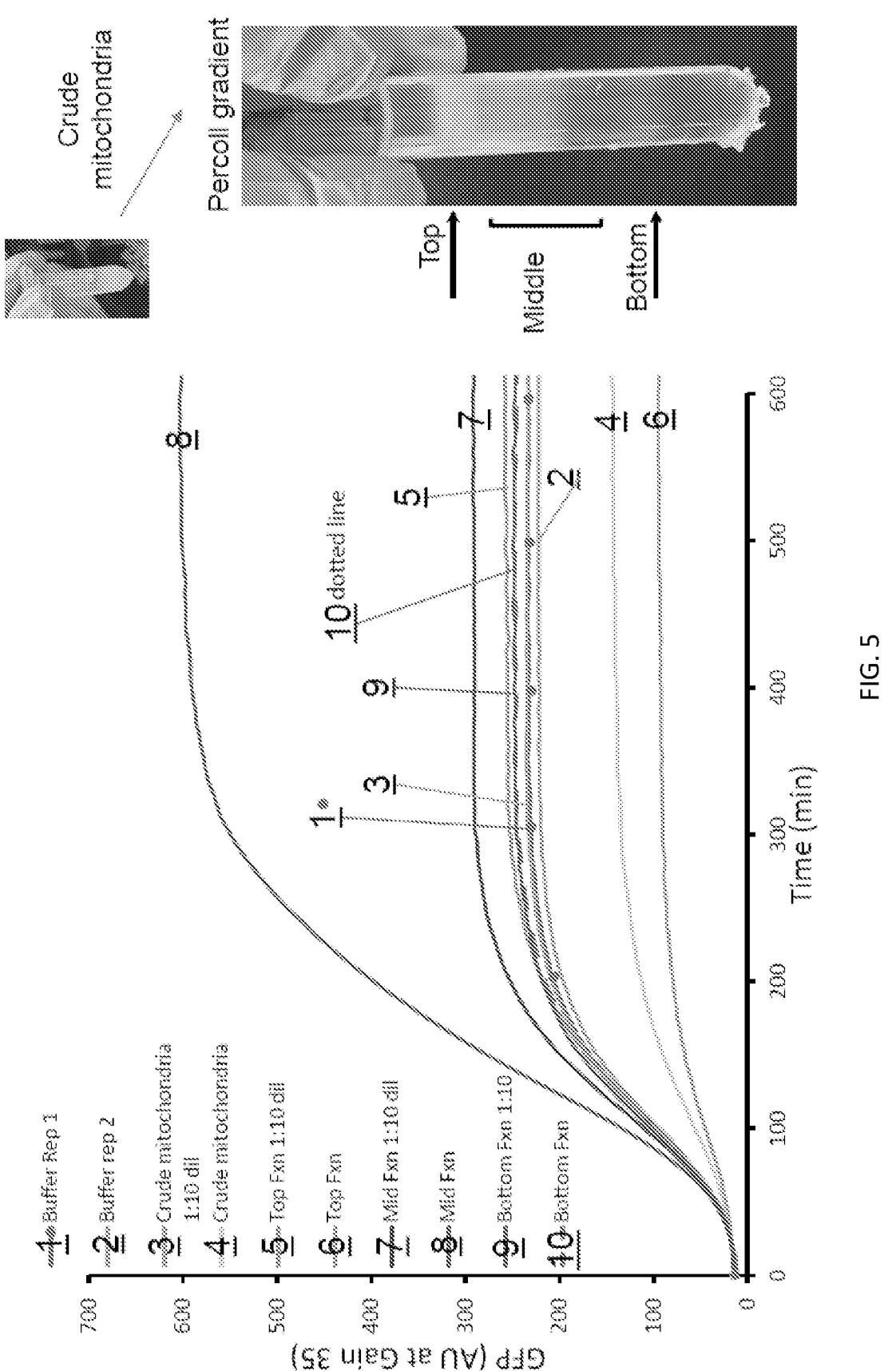
FIG. 5 shows maintenance of homeostasis in a lysate made from tobacco BY2 organisms that are supplemented with crude fractions obtained from a mitochondria preparation from tobacco BY2. Buffer rep. 1 and 2 are controls; crude mitochondria are the substance taken before a Percoll gradient; and fxn (fraction) corresponds to fraction taken after Percoll gradient. 1:10 dilutions indicate 1:10 dilution of the designated fraction. Shown is cell-free expression of a GFP-producing construct to 600 minutes.

Cell-free reactions were then run with different separations from the mitochondria preparation. Cell-free reactions contained 40 mM Hepes-KOH, pH 7.8, 8.5 mM Mg Glutamate, 3 mM ATP, 1.2 mM CTP/UTP/GTP, 30 mM Creatine phosphate, 50 ng/ul T7 RNAP, 50 ug/ml Creatine kinase, 1 mM amino acids, and 80 ng/ul DNA plasmid template containing a T7 promoter, TMV 5' UTR/Omega, sfGFP cDNA, and TMV 3' UTR. BY2 lysate was added at 48% v/v of the reaction in buffer containing 30 mM Hepes-KOH, pH 7.4, 60 mM K glutamate, 0.5 mM Mg Glutamate, and 2 mM DTT. Lastly, reactions were supplemented to 8% final reaction volume with crude fractions, or Percoll separated fractions (top, middle, bottom) in buffer containing 0.3 M sucrose, 1 mM EDTA, and 10 mM MOPS-KOH, pH 7.2. Dilutions (1:10) and mock reactions (buffer only) used the same buffer. Each reaction run at 10 μL in a Nunc 384-well plate at 28° C., and imaged on a Biotek Synergy 2 using 485/ex 528/em filters at gain 35. The results of the cell-free reactions are in FIG. 5. Here, it can be seen that a fraction, "mid fxn," has longer activity than other supplemented fractions or a no fraction control. This is a dose-responsive effect at 1:10 dilution.

Example 2. Mitochondria Purification from Tobacco BY2 Cell Culture

As shown in FIG. 4, mitochondria were purified from Tobacco BY2 cell culture. Tobacco BY2 cells were grown in culture to mid-log phase and harvested by filtration using 2 layers of Miracloth fabric. Protoplasts were isolated from whole plant cells by digestion with Enzyme buffer containing 0.4M Mannitol, 0.7 g/L MES-KOH pH 5.7 with 3% Rohament CL, 0.1% Rohapect UF, 2% Rohapect PL, for 1.5 hours at 25° C. All of the following steps were performed at 4° C., and with ice cold buffers. Protoplasts were centrifuged 5 min, 100 g (no brake), and washed 2 times with Enzyme buffer without the added enzymes. After the second wash, protoplasts were resuspended in approximately an equal volume of Disruption buffer (0.4 M Sucrose, 3 mM EDTA, 50 mM Tris-HCl, pH 7.5, 0.1% BSA, 2 mM DTT (freshly added). The mixture was dounced 15 times with a tight pestle. Lysis was verified by light microscopy. The lysate was centrifuged 3000 g with a fixed angle rotor for 5 min. The supernatant was removed into a fresh 15 ml tube, and then centrifuged 15,600 g in a fixed angle rotor. The supernatant was removed, and the yellow pellet containing crude organelles was saved. The pellet was very gently resuspended in 3 ml Wash buffer (0.3 M Sucrose, 1 mM EDTA, 10 mM MOPS-KOH, pH 7.2). Some of the resuspended pellet was retained and were aliquoted and stored in −80° C. as the crude mitochondrial fraction. This fraction contains mitochondria contaminated by thylakoid or amyloplast membranes, peroxisomes, an endoplasmic reticulum. The remaining fraction was purified by Percoll density gradients. The Percoll gradients were formed in SW41 centrifuge tubes, with 3 ml 40%, 4 ml 23%, and 2 ml 15% Percoll in Wash buffer. Gradients were formed with a Pasteur pipet, loading the 15%, then 23, then 40%, adding each subsequent layer to the bottom of the tube. The tubes were loaded with sample and centrifuged for 15 min at 15,800 rpm with no brake. The resulting gradient had 2 major bands: the top material, and a middle layer of mitochondria. The top layer was discarded, and the middle layer was removed, and was washed with Wash buffer. The washed mitochondria were resuspended in a small volume of Wash buffer, aliquoted, and stored in −80° C. Subsequent dilutions and mock reactions (buffer only) used the same Wash buffer.

Example 3. Mitochondrial Addition to *E. coli* Cell-Free Systems

To test the ability of mitochondria from *Nicotiana tabacum* cv. BY-2 to maintain energy homeostasis and energize TXTL in a heterologous system, an *E. coli* cell-free system without the inverted membrane vesicles necessary for energy homeostasis and without significant substrate-level phosphorylation was generated. Briefly, an *E. coli* cell-free TXTL lysate system was created following methods as described in Sun et al. (2013), with a modification of production using French Press. Inverted membrane vesicles were then removed from the resulting lysate by centrifugation (1 hour at 203,000 relative force of gravity). The removal of these inverted membrane vesicles prevents the system from conducting oxidative phosphorylation as a primary energy source. In addition, the centrifugation at 203,000 relative force of gravity sediments many ribosomes and polysomes that enable translation to occur. An energizing buffer is used as described in Sun et al. (2013), but it is devoid of 3-PGA, such that the resulting TXTL system is unable to conduct substrate-level phosphorylation as the primary energy source. Notably, the buffer retains glutamate. The resulting system is considered a "minimal" system.

Figure 6:
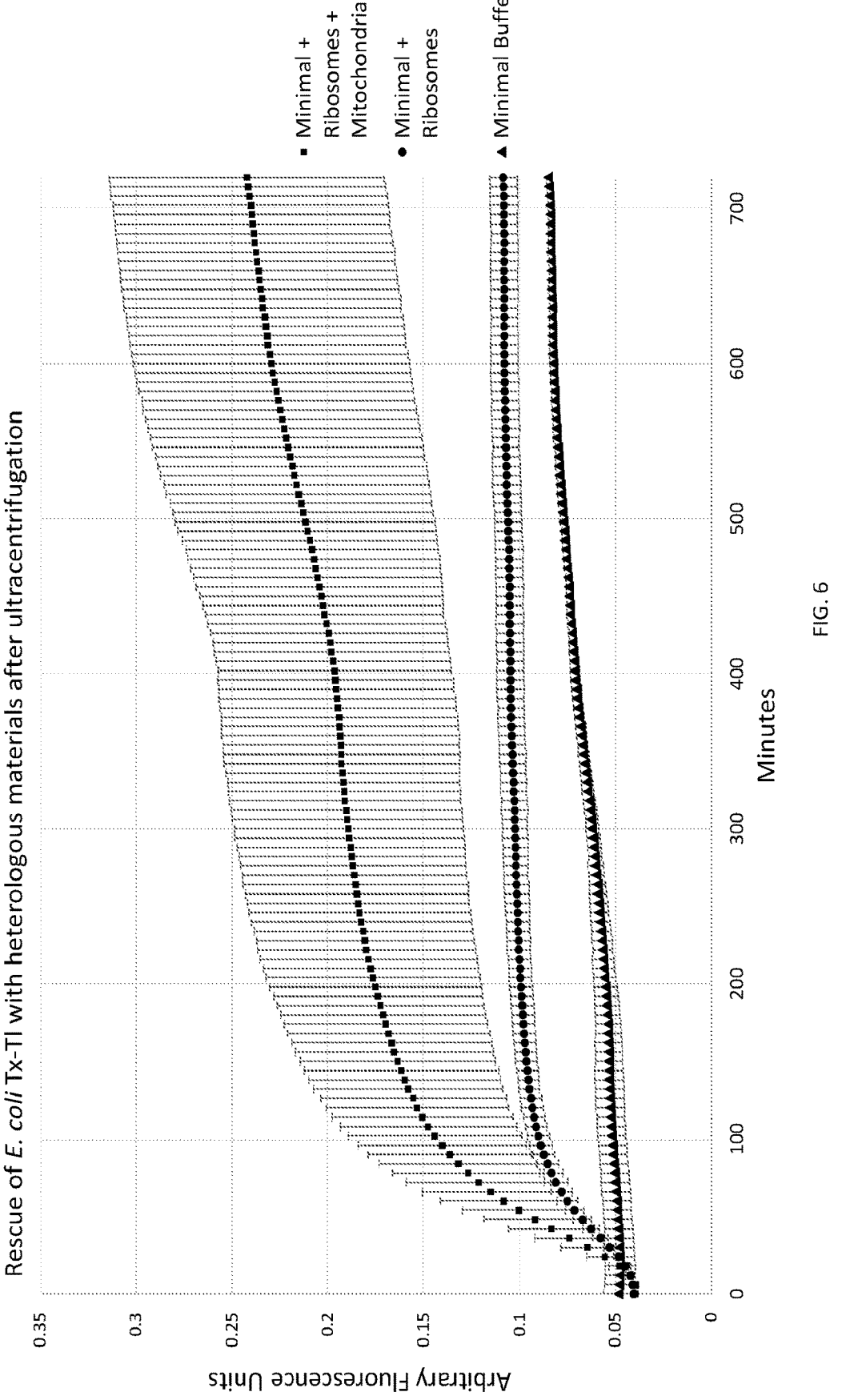
FIG. 6 shows cell-free TXTL production of GFP in *E. coli* lysates with the addition of buffer only, buffer+ribosomes, as compared to buffer+ribosomes+mitochondria.

Cell-free TXTL reactions were then run containing 30% v/v of this lysate, a DNA template for GFP, gamS, and up to 10% v/v *Nicotiana tabacum* cv. BY-2 mitochondria and up to 1.33 uM purified *E. coli* 70S ribosomes. Each reaction was run at 10 µL in a Nunc 384-well plate at 28° C., and imaged on a Biotek Synergy 2 using 485/ex 528/em filters at gain 35." FIG. 6 shows three conditions that are run: one with no addition of BY-2 mitochondria and solely buffer (e.g. minimal buffer), one with no addition of BY2 mitochondria and ribosomes (e.g. minimal+ribosomes), and one with addition of both BY2 mitochondria and of ribosomes (e.g. minimal+ribosomes+mitochondria) (points on FIG. 6 represent the average of n=3 replicates; error bars are the 95% confidence interval around the mean). These conditions demonstrate that the "minimal buffer" minimal system is unable to sustain significant GFP production. When ribosomes are added back in to enable greater translation, partial activity can be recovered but reaction times end within 120 minutes and yields are low, suggesting limitations of ATP regeneration. However, when mitochondria are added in tandem, reaction times recover past 700 minutes and expression rates are high and remain high. This suggests that the mitochondria supplementation is able to rescue a "minimal" *E. coli* cell-free system; surprisingly, the supplementation source is from *Nicotiana tabacum* cv. BY2 mitochondria, which are extremely genetically dis-similar from *E. coli*.

Figure 7:
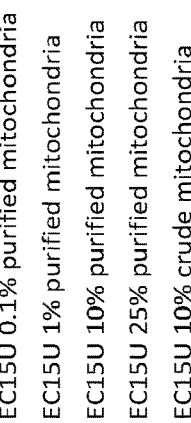
FIG. 7 illustrates that supplementing with mitochondria improved *E. coli* cell-free expression of GFP.

FIG. 7 further demonstrates that supplementing with *Nicotiana tabacum* cv. BY2 mitochondria are the source of improved *E. coli* cell-free expression. By dosing the amount of purified mitochondria, a clear dosage-dependence relationship can be seem from 0.1%-1% v/v purified mitochondria showing little effect on cell-free expression duration and length while 10% and 25% v/v purified mitochondria show increased cell-free expression duration and length. Lower and upper limits can be established, where the effect of purified mitochondria is negligible. In addition, crude purifications of mitochondria did not show a improvement effect; the effect of the buffer in which the mitochondria are stored may negate the positive effect of the mitochondrial addition if the buffer is toxic to transcription, translation, or other cell-free functions.

Figure 8:
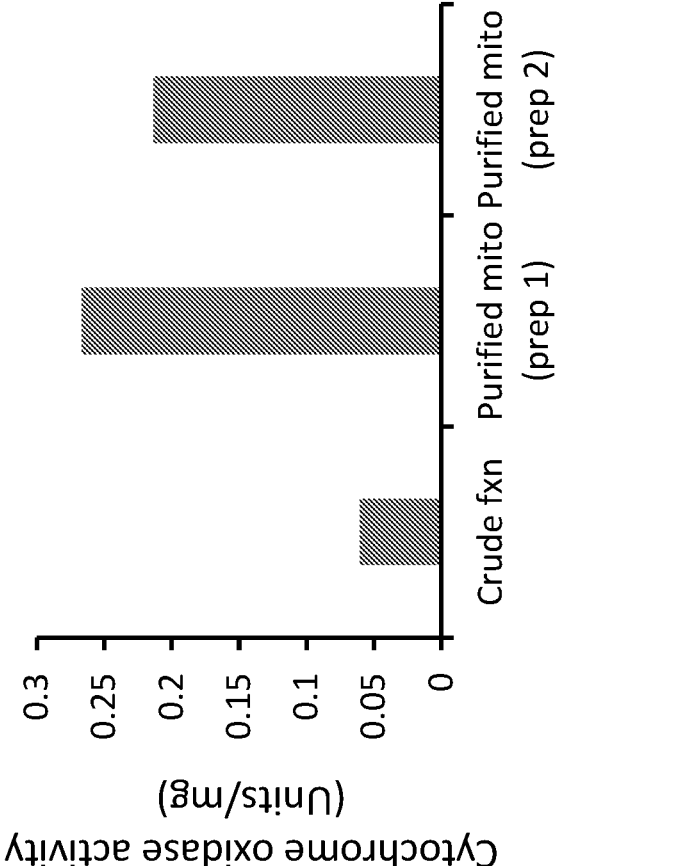
FIG. 8 illustrates the Cytochrome oxidase activity of BY2 crude and purified mitochondria.

Example 4. Cytochrome Oxidase Activity of BY2 Crude and Purified Mitochondria FIG. 8 illustrates the Cytochrome oxidase activity of BY2 crude and purified mitochondria. Mitochondria activity was measured as in Example 5, except that the total protein from crude and purified mitochondrial preps was quantified using a Bradford reagent with bovine serum albumin as a protein standard. The purified mitochondria were 5-10 mg/ml, and the crude fraction was 5.0 mg/ml. The Cytochrome c oxidase activity is presented as a function of units of activity per mg of extract. Our results show that the purified mitochondria preparations had a 3.5-4.4-fold higher specific activity compared to the crude fraction.

Example 5. Determination of Mitochondria Integrity and Activity

Figure 9:
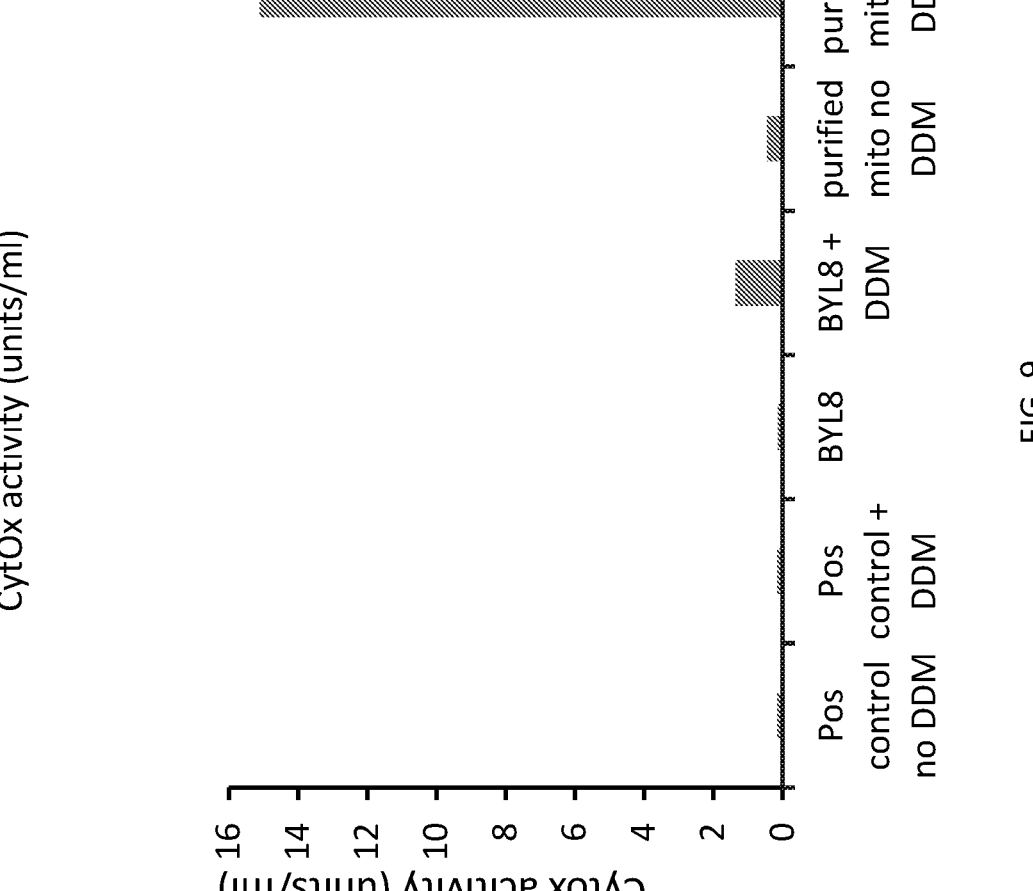
FIG. 9 shows that mitochondria integrity and activity was determined indirectly by measuring Cytochrome c oxidase activity.

As shown in FIG. 9, mitochondria integrity and activity was determined indirectly by measuring Cytochrome c oxidase activity. Cytochrome c oxidase is the principle terminal oxidase of high affinity oxygen in the aerobic metabolism of all animals, plants, yeasts, and some bacteria. A kit (Sigma, CYTOCOX1) was used to measure mitochondrial activity. Briefly, a ferrocytochrome c substrate solution was made by reducing cytochrome C with a dithiothreitol solution. Reduction was confirmed by comparing the ration of $A_{550}/A_{565}$ ratio as greater than 10. The absorption of cytochrome c at 550 nm changes with its oxidation state. Reactions were performed in a cuvette at 25° C. and followed the kinetic decrease in $A_{550}$. One unit is defined by the ability to oxidize 1.0 µmole of ferrocytochrome c per minute at pH 7.0 at 25° C. A positive control cytochrome c oxidase was used to determine that the assay was working as described. Further, the kit allows the determination of mitochondrial outer membrane integrity by comparing Cytochrome C activity with and without addition of the detergent, n-Dodecyl B-D-maltoside (DDM). Notably, the positive control is not affected by DDM addition. Our results show that BYL8 contained a small number of active mitochondria, but the highest activity was observed with the purified mitochondria. Mitochondria with undamaged membranes were 90% (BYL8) and 97% (purified mitochondria).

Example 6. Analyzing BY2 Crude and Purified Mitochondria

Figure 10:
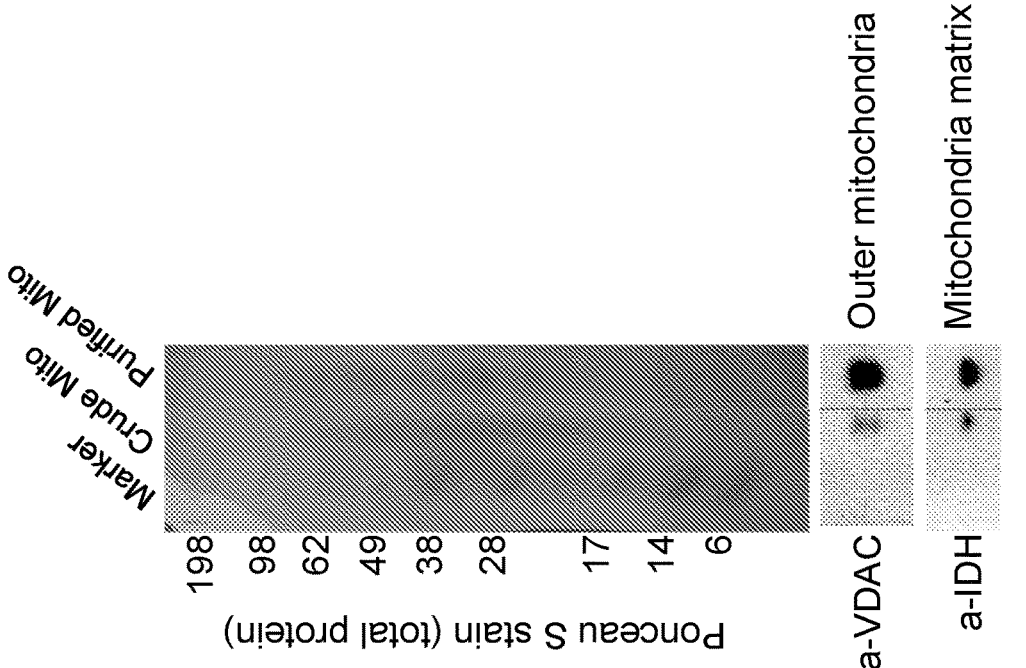
FIG. 10 shows a crude preparation including mitochondria and a purified mitochondria preparation, as analyzed by protein staining and a Western Blot.

As shown in FIG. 10, BY2 crude and purified mitochondria were analyzed using a Western Blot. Total protein (20 ug) was separated by SDS-PAGE and transferred to nitrocellulose membranes. Membranes were stained with Ponceau S to verify transfer, and then blocked with non-fat milk. Membranes were probed with primary antibodies specific to mitochondria, including anti-VDAC (voltage-dependent anion selective channel protein 1) of the outer mitochondrial membrane protein porin 1 (Agrisera AS07 212, anti-rabbit polyclonal antibody, 1:5000 dilution), and anti-IDH (Isocitrate dehydrogenase) of the plant NADH dependent isocitrate dehydrogenase located in the mitochondrial matrix (Agrisera AS06 203A, anti-rabbit polyclonal antibody, 1:2500 dilution). The secondary antibody used was anti-rabbit HRP (1:5000), followed by detection by enhanced chemiluminescence and Versadoc imaging (Biorad). As expected, the crude and purified fractions stained positive for mitochondria markers, VDAC1 and IDH. However, the purified mitochondria had darker bands of mitochondrial proteins for the same protein loaded, indicating a significantly higher specific activity.

Example 7. Production of the Terpenoid Precursor Mevalonate from Acetyl CoA

In a reaction, 10 mM of acetyl CoA can be supplied as the substrate. The enzymes acetoacetyl-CoA thiolase, HMG-CoA synthase, and HMG-CoA reductase will also be supplied to the reaction as purified components at 7.5 mg/mL. The genetic sequences for these enzymes, with a His6 tag, will be cloned into a protein production vector (e.g. pET vector), followed by transformation into an *E. coli* strain and selection for the strain carrying the plasmid. 100 mL of each strain will then be grown to a mid-log OD, induced, lysed using mechanical techniques, and then the protein will be purified from the lysis using Ni-NTA resin and stored in a salt buffer with glycerol cryoprotectant. The reaction will also be supplemented by 50 mM Tris-Cl pH 7.5, 5 mM Magnesium glutamate, 5 mM Potassium glutamate, 0.5 mM NAD+, 0.5 mM NADP+, 1 mM CoA, 10 mM inorganic phosphate, 0.1 mM pyrophosphate, 1 mM DTT. In addition, to provide cofactor balance and generate additional acetyl CoA the reaction can be supplemented with 7.5 mg/mL of hexokinase, phosphoglucose isomerase, phosphofructoki- nase, aldoase, triose phosphate isomerase, glyceraldehyde 3-phosphate dehydrogenase, phosphoglycerate kinase, phosphoglyceromutase, enolase, pyruvate kinase, pyruvate dehydrogenase (complex), 100 mM of glucose, 2 mM of ATP, 2 mM of ADP, 0.25 mM 2,3 biphosphoglycerate, 1 mM FBP.

In the above reaction, a comparison can be made with those with supplemented mitochondria at 2.5 mg/mL and those without supplemented mitochondria. It is expected that the reaction with supplemented mitochondria should make the same or more mevalonate than that without supplemented mitochondria. In addition, reaction with supplemented mitochondria should make mevalonate for at or longer periods of time than that without supplemented mitochondria. Furthermore, the use of additional enzymes, such as NADH oxidase or metagenomic variants of *E. coli* glyceraldehyde 3-phosphate dehydrogenase, may also extend reaction period by providing an artificial homeostasis balance. It would be expected that the improvement by using mitochondria would be similar to the improvement by providing artificial homeostasis balance.

Example 8. Production of GFP from a DNA Template in a HeLa Cell-Free System Supplemented with Mitochondria and/or Chloroplasts HeLa S3 cells were cultured in spinner flasks at 37° C. in S-MEM media supplemented with 10% fetal calf serum, penicillin (1 unit/mL), and streptomycin (0.1 mg/mL) and GlutaMAX (2 mM). The cells were harvested with cell density between 0.8-1.5×$10^6$ cells/ml. The cells were col- lected by centrifugation at about 1200 rpm. The cell pellets were washed three times with ice cold Wash Buffer con- taining 35 mM HEPES-KOH, pH 7.5, 140 mM NaCl, and 11 mM glucose, and one time in Extraction Buffer containing 20 mM HEPES-KOH, pH 7.5, 45 mM potassium acetate, 45 mM KCl, 1.8 mM magnesium acetate, and 1 mM Dithio- threitol. The cell pellet was resuspended in an equal volume of the extraction buffer to 3.0×$10^8$ cells/ml. The resuspended solution was disrupted using a French press. The resulting lysate was mixed with ⅟₂₉ volume of the high potassium buffer containing 20 mM HEPES-KOH, pH 7.5, 945 mM potassium acetate, 945 mM KCl, 1.8 mM magnesium acetate, and 1 mM DTT. The homogenate was then centri- fuged twice at 1,200×g for 5 min at 4° C. and the supernatant was recovered. The final extract was 26 mg/ml, aliquoted, frozen in liquid nitrogen, and stored at −80° C.

HeLa extract can then be combined with a buffer and a T7-GFP expressing plasmid, such as pT7CFE1-Chis with a subcloned GFP, to enable cell-free transcription and trans- lation. In particular, 12.5 uL of a HeLa extract can be combined with 2.5 uL of accessory proteins (e.g. recombi- nant K3L, recombinant GADD34), 5 uL of a reaction mix, 2 uL of pT7CFE1-Chis with a subcloned GFP at 0.5 mg/mL, and 3 uL of water for a 25 uL reaction. The final concen- trations of the reaction is 50% v/v HeLa extract, 0.83 mM GTP, CTP, and UTP, 1.25 mM ATP, 20 mM creatine phos- phate, 60 ug/mL creatine kinase, 90 ug/mL calf liver tRNA, 8-120 uM of 20 amino acids, 3.8 mM-8.5 mM of magnesium glutamate, 100-180 mM of potassium glutamate plus KCl, 54 mM of HEPES-KOH, 11.1 ug/mL T7 RNA polymerase, 0.5 mM spermidine, and recombinant K3l and recombinant GADD34 titrated and added to optimum activity levels. This is the "HeLa cell-free system." Ranges are given in some areas as the cell-free system will need to be optimized, especially in the amounts of magnesium glutamate, potas- sium glutamate plus KCl, recombinant K3l, and recombi- nant GADD34 as each HeLa extract preparation will result in different amounts of magnesium and potassium require- ments to enable transcription and translation.

Importantly, the HeLa cell-free system will need to con- tain a source of glutamate at mM concentrations, which can be used as a substrate for added mitochondria to conduct oxidative phosphorylation. This can be provided by substi- tuting glutamate salts for acetate salts. Two conditions will then be tested: in one condition, the HeLa cell-free system is supplemented with titrated amounts of 0.1 to 25% v/v *Nicotiana tabacum* cv. BY-2 mitochondria; in another con- dition, the HeLa cell-free system contains no added mito- chondria. GFP production can then be tracked in a microtiter plate reader (e.g. 25 µL in a Nunc 384-well plate at 32° C., and imaged on a Biotek Synergy 2 using 485/ex 528/em filters at gain 35). The condition where *Nicotiana tabacum* cv. BY-2 mitochondria is titrated into the reaction should show equal or greater rates of cell-free expression as well as an equal or greater amount of GFP produced. It will be important to ensure that the mitochondria are extremely pure, such that the buffer in which it is stored as well as any ancillary proteins present in the mitochondria preparation do not interfere or interact with the HeLa transcription and translation process.

This result can show that the addition of mitochondria to HeLa cell-free systems can improve cell-free expression rates and/or production amounts.

Other heterologous organelles such as chloroplasts can also be added to the HeLa cell-free system. For the addition of chloroplasts, purified *Arabidopsis* chloroplasts can be obtained by following the method of (Seigneurin-Berny 2008) and transferred to a buffer which is devoid of inhibi- tors to cell-free transcription and translation. Right before usage, 0.5 mM of ATP can be optionally added to the solution to start chloroplast activity. Purified chloroplasts can then be added to the aforementioned HeLa cell-free system in lieu of *Nicotiana tabacum* cv. BY-2 mitochondria. Four conditions can then be tested: in one condition, the HeLa cell-free system is supplemented with titrated amounts of 0.1 to 25% v/v *Arabidopsis* chloroplasts and is run in light conditions from an incandescent source; in another condi- tion, the chloroplasts are titrated but run in the dark, in another condition, the HeLa cell-free system contains no added chloroplast and run in light conditions from an incandescent source; in a final condition, the HeLa cell-free system contains no added chloroplast and run in the dark. GFP production can then be tracked in a microtiter plate reader (e.g., 25 µL in a Nunc 384-well plate at 32° C., and imaged on a Biotek Synergy 2 using 485/ex 528/em filters at gain 35). The condition where *Arabidopsis* chloroplasts is titrated into the reaction should show equal or greater rates of cell-free expression as well as an equal or greater amount of GFP produced. This will occur in either the light or the dark condition.

EQUIVALENTS

The present disclosure provides among other things com- positions and methods disclosed herein relate to protecting input nucleic acid templates in vitro transcription/translation (TXTL) systems. While specific embodiments of the subject disclosure have been discussed, the above specification is illustrative and not restrictive. Many variations of this disclosure will become apparent to those skilled in the art upon review of this specification. The full scope of the disclosure should be determined by reference to the claims, along with their full scope of equivalents, and the specification, along with such variations.

INCORPORATION BY REFERENCE

All publications, patents and sequence database entries mentioned herein are hereby incorporated by reference in their entirety as if each individual publication or patent or sequence database entry is specifically and individually indicated to be incorporated by reference.

REFERENCES

Blaskovich, M. A. T., 2016. Unusual Amino Acids in Medicinal Chemistry. *Journal of medicinal chemistry*, 59(24), pp. 10807-10836.

Buntru, M. et al., 2014. Tobacco BY-2 cell-free lysate: an alternative and highly-productive plant-based in vitro translation system. *BMC biotechnology*, 14(1), p. 37.

Chiao, A. C., Murray, R. M. & Sun, Z. Z., 2016. Development of prokaryotic cell-free systems for synthetic biology. *bioRxiv*, p. 048710.

Jewett, M. C. & Swartz, J. R., 2004. Mimicking the *Escherichia coli* cytoplasmic environment activates long-lived and efficient cell-free protein synthesis. *Biotechnol Bioeng*, 86(1), pp. 19-26.

Karim, A. S. & Jewett, M. C., 2016. A cell-free framework for rapid biosynthetic pathway prototyping and enzyme discovery. *Metab Eng*, 36, pp. 116-126.

Kelwick, R. et al., 2016. Development of a *Bacillus subtilis* cell-free transcription-translation system for prototyping regulatory elements. *Metab Eng*, 38, pp. 370-381.

Kigawa, T. et al., 1999. Cell-free production and stable-isotope labeling of milligram quantities of proteins. FEBS Lett. 1999 Jan. 8; 442(1):15-9.

Kim, D.-M. & Swartz, J. R., 2001. Regeneration of adenosine triphosphate from glycolytic intermediates for cell-free protein synthesis. *Biotechnol Bioeng*, 74(4), pp. 309-316.

Komoda, K., Naito, S. & Ishikawa, M., 2004. Replication of plant RNA virus genomes in a cell-free extract of evacuolated plant protoplasts. *Proceedings of the National Academy of Sciences of the United States of America*, 101(7), pp. 1863-1867.

Meyer, E. H. & Millar, A. H., 2008. Isolation of Mitochondria from Plant Cell Culture. In *2D PAGE: Sample Preparation and Fractionation*. Humana Press, pp. 163-169.

Niederholtmeyer, H. et al., 2015. Rapid cell-free forward engineering of novel genetic ring oscillators. *eLife*.

Opgenorth, P. H., Korman, T. P. & Bowie, J. U., 2014. A synthetic biochemistry molecular purge valve module that maintains redox balance. *Nature Communications*, 5, p. 998.

Shin, J. & Noireaux, V., 2012. An *E. coli* Cell-Free Expression Toolbox: Application to Synthetic Gene Circuits and Artificial Cells. *ACS Synth Biol*, 1(1), pp. 29-41.

Sun, Z. Z. et al., 2014. Linear DNA for Rapid Prototyping of Synthetic Biological Circuits in an *Escherichia coli* Based TXTL Cell-Free System. *ACS Synth Biol*, 3(6), pp. 387-397.

Sun, Z. Z. et al., 2013. Protocols for Implementing an *Escherichia Coli* Based TXTL Cell-Free Expression System for Synthetic Biology. *Journal of Visualized Experiments*, e50762(79), pp. e50762-e50762.

Seigneurin-Berny, et al., 2008. Purification of Intact Chloroplasts from *Arabidopsis* and Spinach Leaves by Isopycnic Centrifugation. *Curr. Protoc. Cell Biol*. Chapter 3: Unit 3.30. doi: 10.1002/0471143030.cb0330s40.

Takahashi, M. K. et al., 2015. Characterizing and prototyping genetic networks with cell-free transcription-translation reactions. *Methods*.

Thompson, J., Rae, S. & Cundliffe, E., 1984. Coupled transcription-translation in extracts of *Streptomyces lividans*. *Molecular and General Genetics MGG*, 195(1-2), pp. 39-43.

The invention claimed is:

1. A composition, comprising:
   a cell-free extract obtained from an organism, wherein said organism is *E. coli;*
   a nucleic acid; and
   an organelle that is heterologous to the organism, wherein said heterologous organelle is a mitochondria.

2. The composition of claim 1, wherein the cell-free extract is present at a concentration of about 0.005-1000 mg/ml, 0.05-500 mg/ml, 0.5-100 mg/ml, or 1-20 mg/ml, wherein the extract has been at least partially purified.

3. The composition of claim 1, wherein the nucleic acid comprises a linear DNA or a plasmid DNA or an RNA.

4. The composition of claim 1, wherein the nucleic acid comprises a template nucleic acid for expression into a desired RNA or protein product.

5. The composition of claim 1, wherein the organelle comprises intact organelle and/or non-intact organelle, wherein in the non-intact organelle, an outer membrane and/or inner membrane of the organelle have been at least partially disrupted.

6. The composition of claim 1, wherein the organelle is present at a concentration of about 0.000015-100 mg/ml, 0.00015-50 mg/ml, 0.0015-10 mg/ml, or 0.15-4.5 mg/ml.

7. The composition of claim 1, wherein the organelle is at least partially purified, and is stored in a solution free of inhibitors to cell-free transcription and translation.

8. The composition of claim 1, wherein a ratio of the extract to the organelle by weight is between about 100,000,000:1 and 0.00005:1; between 600,000:1 and 0.005:1; between 300:1 and 0.05:1; or between 10:1 and 0.2:1.

9. The composition of claim 1, wherein the organelle is obtained from eukaryotic cells.

10. The composition of claim 1, further comprising cofactors, enzymes, and other reagents for transcription and/or translation.

11. The composition of claim 1, further comprising a substrate capable of entering the TCA cycle.

12. The composition of claim 1, wherein said mitochondria is from *Nicotiana tabacum* cv. BY-2 cells.

\* \* \* \* \*